United States Patent [19]

Erdmann et al.

[11] 4,179,218
[45] Dec. 18, 1979

[54] PARTICLE SIZE ANALYZER

[75] Inventors: Joachim C. Erdmann, Seattle; Robert I. Gellert, Redmond; Richard L. Skaugset, Kennewick, all of Wash.

[73] Assignee: The Boeing Company, Seattle, Wash.

[21] Appl. No.: 905,793

[22] Filed: May 15, 1978

[51] Int. Cl.$^2$ ............................................. G01N 21/26
[52] U.S. Cl. .................................... 356/336; 250/574; 356/28.5
[58] Field of Search ............... 356/335, 336, 337, 338, 356/342, 28.5; 250/574

[56] References Cited

U.S. PATENT DOCUMENTS

| 3,680,961 | 8/1972 | Rudd | 356/335 |
| 3,830,568 | 8/1974 | Allen | 356/336 X |

OTHER PUBLICATIONS

*Applied Optics*, vol. 12, No. 6, Jun. 1973, pp. 1145–1156, Brayton et al, "Two-Component Dual Scatter Laser Doppler Velocimeter with Frequency Burst Signal Readout".

*Primary Examiner*—John K. Corbin
*Assistant Examiner*—B. Y. Arnold
*Attorney, Agent, or Firm*—Christensen, O'Connor, Johnson & Kindness

[57] ABSTRACT

A particle size analyzer that measures the intensity of light scattered by moving particles passing through the probe of a crossed beam laser anemometer, verifies that the measured signal was produced by a particle passing through a region near the center of the probe, and stores count values related to the number of particles producing the same scattered light intensity value is disclosed. Since scattered light intensity values are related to particle size, the stored count values equal the number of particles of the same size detected by the analyzer. In the preferred form of the invention, the measured light intensity determines the address of a particular intensity bin of a storage system. After verification to determine if a measured intensity value was produced by a particle passing through a region near the center of the probe, the count value stored in an intensity bin related to the measured value is updated by one. When any bin reaches the maximum value that can be stored therein, the particle light intensity measuring mode of operation ends and the particle size analyzer is placed in a readout mode of operation. In the readout mode of operation, the intensity bin count values are sequentially read out, converted into analog form, and displayed.

16 Claims, 12 Drawing Figures

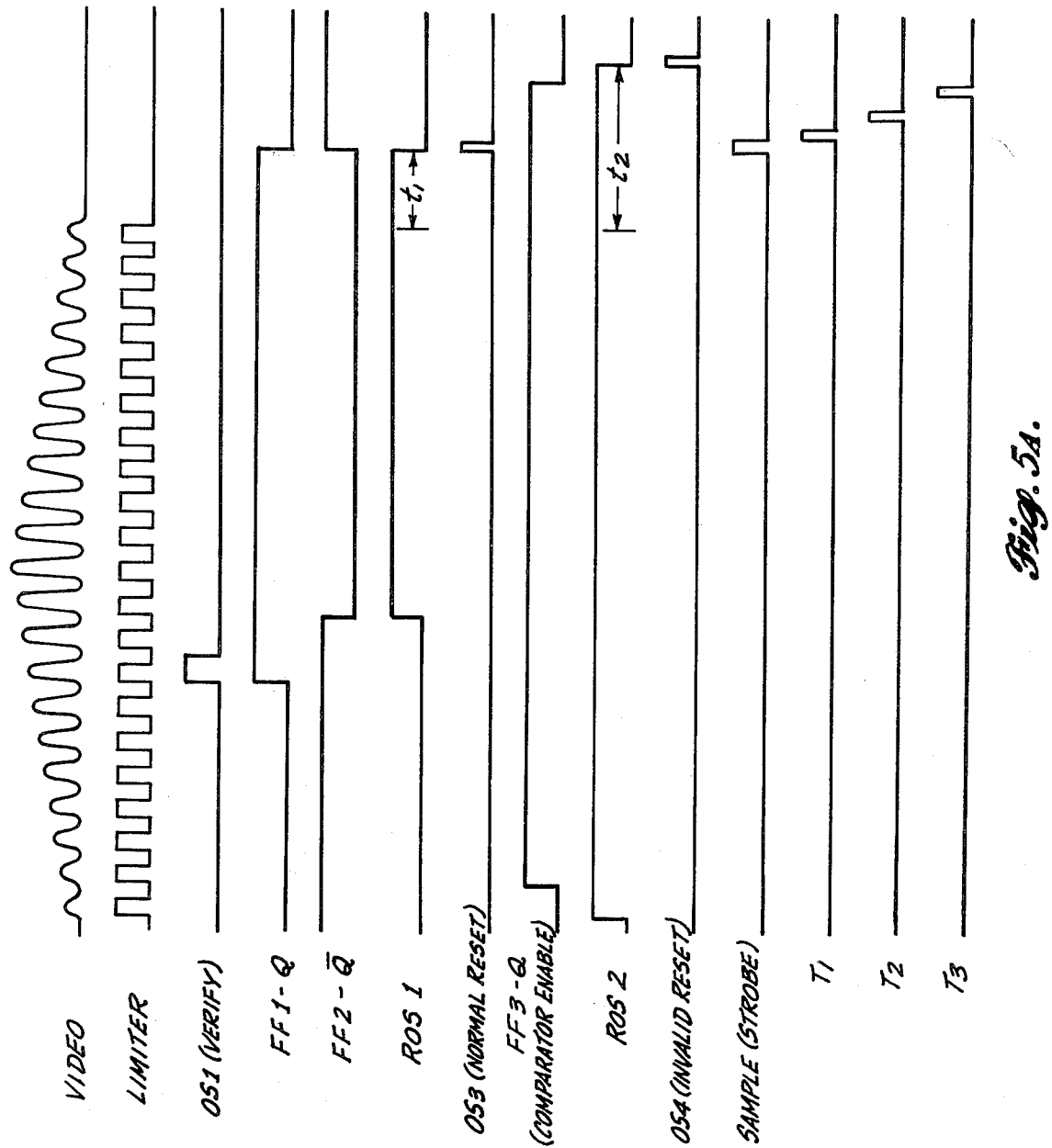

PARTICLE SIZE ANALYZER

BACKGROUND OF THE INVENTION

This invention relates to analyzers and, more particularly, to analyzers for determining the numbers of particles of different sizes in a stream of particles.

In certain environments, it is desirable to measure micron sized particles at high rates, e.g., rates in the order of tens of thousands per second. It is also desirable, in certain environments, to categorize the measured particles in accordance with size and provide an output that indicates the number of particles of each size that have been detected and measured. In the past, this result usually has been accomplished by pumping a sample into an instrument for analysis. Examples of such analyzers are the Model 3030 sold by Thermo Systems, Inc., of St. Paul, Minn., and the Model PC-320 sold by HIAC Instrument Company of Montclair, Calif.

The primary disadvantage of instruments requiring that a sample be pumped into the instrument for analysis is their inability to measure particle size in situ, i.e., in free jet streams, clouds, outside aircraft, inside environmental chambers, etc. Moreover, such devices are entirely unsuitable for use in certain environments, such as the Jovian atmosphere, for example. As a result, a need exists for a noncontacting particle size analyzer that does not require that particles be pumped or drawn into a container for analysis.

Therefore, it is an object of this invention to provide a new and improved particle size analyzer.

It is a further object of this invention to provide a noncontacting particle size analyzer that measures particle size without requiring that the particles be drawn into a chamber for measurement.

It is yet another object of this invention to provide a particle size analyzer suitable for determining the size of particles in situ, and providing an output that indicates the number of particles of different sizes that have been detected over a fixed or variable time period.

SUMMARY OF THE INVENTION

In accordance with this invention, a particle size analyzer that measures the intensity of light scattered by moving particles and stores count values related to the number of particles producing the same scattered light intensity is provided. Since scattered light intensity is related to particle size, the count values equal the number of particles of the same size detected by the analyzer.

In the past, crossed beam laser anemometers have been used to measure, in a noncontacting manner, the velocity of particles in situ. A crossed beam laser anemometer includes a laser whose output is split into two separate beams. The separate beams are redirected such that they cross. In the regions where the beams cross, a series of fringes are formed. The fringes form a noncontacting "probe" (i.e., the probe is noncontacting in physical sense) and particles passing through the probe scatter light. The scattered light is detected and, if an adequate number of fringes are intersected, analyzed to provide an indication of the velocity of the particles passing through the probe.

The preferred form of the present invention includes a crossed beam laser anemometer, or selected components of a laser anemometer. The signals produced by the laser anemometer as a result of particles passing through the probe are analyzed and the results used to provide a histogram of particle number versus size that can be displayed on an oscilloscope or other display device, or recorded on a suitable recording medium. In this regard, the invention provides a system for measuring only the scattered light produced by particles passing through a region near the center of the probe. Light scattered by particles passing through the outer regions of the probe is rejected, i.e., not measured. Measured light intensity values are used to determine the address of a related intensity bin of a storage system. Each time a particular light intensity is measured, the count value stored in the related density bin is updated by one. Preferably, the intensity bins are read out when any one of the intensity bins reaches a maximum value. Alternatively, the bins may be automatically read out at predetermined time intervals. In any event, when readout occurs, particle light intensity measuring ends. In the readout mode of operation, the intensity bin count values are sequentially read out, converted into analog form and displayed (or recorded).

In the most presently preferred form of the invention, whether or not the scattered light from a particular particle is to be measured is determined by counting a series of pulses created by and related to the number of fringes through which the particle passes. Since the number of fringes located at the center of the probe is greater than the number of fringes located near the outer regions of the probe, the number of pulses determines how close the particle is to the center of the probe. Only pulse count values above a predetermined number allow the scattered light to be measured. As a result, only particles passing near the center of the probe are counted. Also, in this preferred form of the invention, the count values are stored in the bins of a random access memory (RAM). Each time a particular scattered light intensity value measurement is made, the number stored in the related bin of the RAM is read out into a counter. Thereafter, the counter value is updated by one and the count value reinserted into the same bin of the RAM. During readout, the RAM bins are sequentially addressed. As the bins are addressed, their values are converted from digital form to analog form and the result applied to a display (or recorded). Further, the values stored in the RAM bins can be displayed on a real time basis by reading, converting and displaying bin values as they are updated.

It will be appreciated from the foregoing summary that the invention provides a particle size analyzer suitable for analyzing light scattered by particles in accordance with size, storing counts of the number of particles of particular sizes detected by the analyzer, and selectively displaying the stored count values. The display is a histogram of particle number versus size and can be shown on any suitable display medium, such as an oscilloscope. Alternatively, the histogram can be recorded in either visually readable form or in machine readable form. While the preferred form of the invention uses a readily available crossed beam laser anemometer, it will be appreciated that such a laser anemometer produces additional output signals that are not necessarily needed by the present invention. As a result, a simplified version of a crossed beam laser anemometer can be used with the counting, storing and display subsystems of the present invention, if desired.

BRIEF DESCRIPTION OF THE DRAWINGS

The foregoing objects and many of the attendant advantages of this invention will become more readily appreciated as the same becomes better understood by reference to the following detailed description when taken in conjunction with the accompanying drawings wherein:

FIGS. 5A and 5B are timing diagrams used to assist in describing the operation of the sample control illustrated in FIG. 4;

DESCRIPTION OF THE PREFERRED EMBODIMENT

As will be better understood from the following discussion, the invention comprises a system for analyzing signals of the type produced by a crossed beam laser anemometer. The analysis is such that particle size is determined and a histogram of particle number versus particle size is provided.

Figure 1:
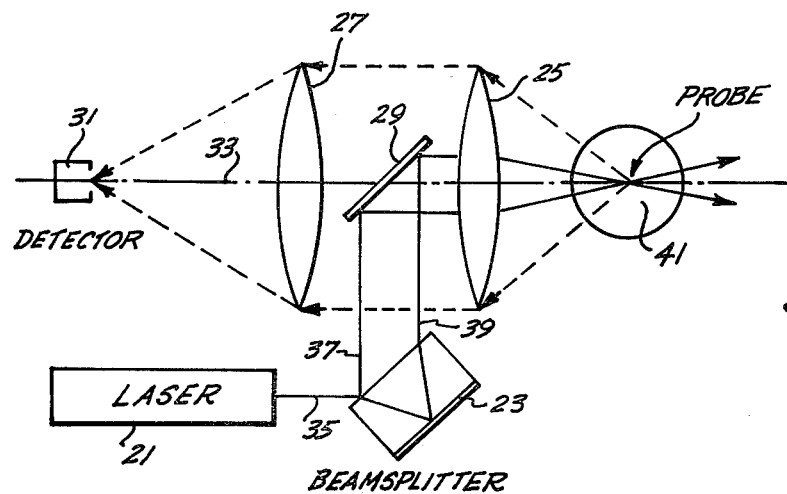
FIG. 1 is a pictorial diagram of a crossed beam laser anemometer.

FIG. 1 is a pictorial diagram of the main components of a laser anemometer included in the preferred embodiment of the invention and comprises: a laser 21; a beam splitter 23; first and second focusing lenses 25 and 27; a mirror or prism 29; and, a detector 31. The first and second focusing lenses 25 and 27 are mounted along a common optical axis 33. Mounted between the first and second focusing lenses 25 and 27 is the prism or mirror 29. The prism or mirror 29 is mounted such that its reflective surface forms an angle of 45 degrees with respect to the optical axis 33.

The light beam 35 produced by the laser 21 is directed toward the beam splitter, which may be formed by a coated optical flat. The beam splitter splits the laser beam into two parallel light beams 37 and 39. The laser and the beam splitter 23 are positioned such that the parallel beams lie orthogonal to the optical axis 33 and between the first and second focusing lenses 25 and 27.

The prism or mirror 29 is positioned such that it intersects the two parallel light beams 37 and 39 and bends those light beams by 90 degrees, toward the first focusing lens 25. The first focusing lens 25 not only focuses each beam, it also directs the two beams to a region of intersection, which is located at the focal point of the first focusng lens 25 on the side of the focusing lens opposite to the prison or mirror 29. The region of intersection is defined as the probe 41 of the laser anemometer. Light scattered when a particle traverses the crossover region of the two beams (the probe) in the manner hereinafter described, is collected by the first focusing lens 25 and directed toward the second focusing lens 27. The light is focusing by the second focusing lens onto the light detecting surface of the detector 31. The light detecting surface of the detector may be formed by the photo cathode of a photomultiplier tube, for example.

Figure 2:
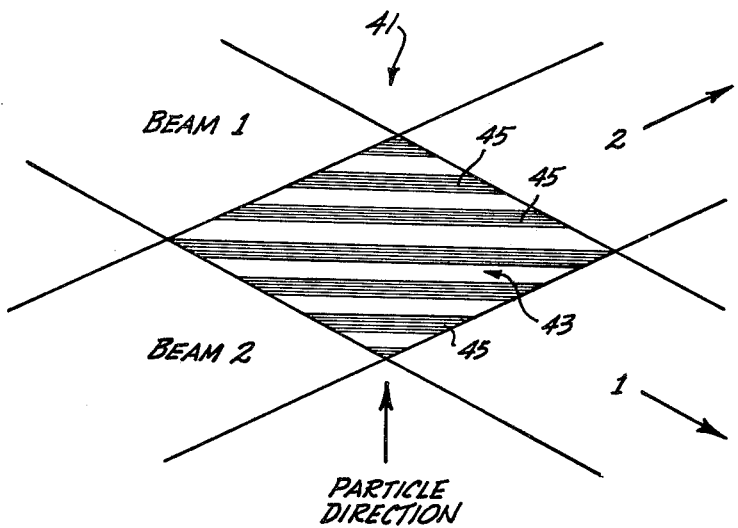
FIG. 2 is an enlarged pictorial diagram of the fringes formed in the probe region of a crossed beam laser anemometer.

FIG. 2 is an exploded view of the beam crossover region (probe) 41. An interference fringe pattern 43 is formed in the probe or beam crossover region by the intersecting beams. The diameter of the probe and the fringe spacing depends on the F-number of the focusing lens and the intersection angle between the two beams. A typical probe diameter is approximately 200 microns. A typical fringe spacing is approximately 5 microns (dark-to-dark spacing). The fringes 45 are actually planar regions in space stacked like boards parallel to the angular bisector of the two beams, with their interfaces at right angles to the plane of the two beams. In this regard, in FIG. 2, the fringes 45 would extend normally to the plane of the figure. As a particle passes through the fringe stack (from bottom to top, as illustrated in FIG. 2), the scattered light is alternately blinked on and off, depending upon whether the particle is in a bright or dark region. The photomultiplier detects this on and off blinking and its output current varies in accordance therewith. Since the fringe spacing is known from the beam angle and the laser wavelength, the particle velocity can be determined by measuring the period of the detector burst (Doppler frequency). These items are related by the formula:

$$v = f_D \cdot \lambda \cdot F$$

where:
v = velocity in cm/s
$f_D$ = signal frequency (doppler) in Hz
$\lambda$ = laser wavelength in cm
F = F - number of focusing lens with respect to beam separation (1/F equals the angle between the beam in radians)

The detector 31 of a laser anemometer, in addition to a photomultiplier, includes electronic circuitry for determining the velocity of the particle based on the observed doppler frequency. The determination is made in a manner that eliminates certain erroneous results. For example, velocity indication errors could occur if the scattered light is alternately blinked on and off by two particles of different velocities traversing the probe volume simultaneously. Alternately, errors could occur if the detected scattered light is caused by a particle passing through the outer region of the probe. In the latter case, errors will occur, if the detector burst period is measured, because the signal level will be too low to be accurately sensed. As a result the laser anemometer detector, as is well known to those familiar with laser anemometers, screens the received signal and discards the output if the detector determines that the received information is likely to be erroneous. In this regard, by comparing the duration of the first four doppler cycles with the duration of the second four, the detector determines whether a single particle or two particles of different velocities created the detected light. If the two time intervals are equal to within a preset tolerance, the data is accepted. Alternatively, if the two time intervals are unequal, the data is rejected. Low signal levels, of course, are discriminated against by using a level detector to detect the level of the signal produced by the received light. In essence, the laser anemometer produces three output signals, a VIDEO signal representing the scattered light that alternately blinks on and off as the particle passes through the probe; a VERIFY signal that indicates that the video signal is an acceptable signal; and, a LIMITER signal. The LIMITER signal is a square wave representation of the scattered light signal, i.e., the square wave signal has a frequency equal to the frequency of the video signal.

The present invention analyzes the output of a laser anemometer and produces a histogram of the number of particles of different size passing through the probe. The invention is based on the fact that the intensity of the scattered light is related to particle size. The magnitude of the video signal, which is directly related to the intensity of the scattered light, is accepted as valid and measured by the invention if the video signal is produced by a single particle crossing an adequate number of fringes. Valid signals cause related particle size bins to be updated and invalid signals are rejected. When any particular bin is full, all of the bins are read out and applied to a display (and/or recording) device. Alternatively, at predetermined fixed intervals, the bin outputs can be applied to a display (and/or recording) device. Still further, a real time display can be provided by reading out bin data each time a bin has its count value increased.

The invention was developed to utilize a conventional laser anemometer which has been modified by adding additional circuitry as hereinafter described so as to make a particle size analyzer apparatus. As will be readily appreciated by those skilled in the art, simplified versions of the electronic subsystems (e.g., simplified versions of the electronic circuitry used to prevent erroneous results) can be incorporated in and form a part of the electronic subsystem of the invention, if desired.

Figure 3:
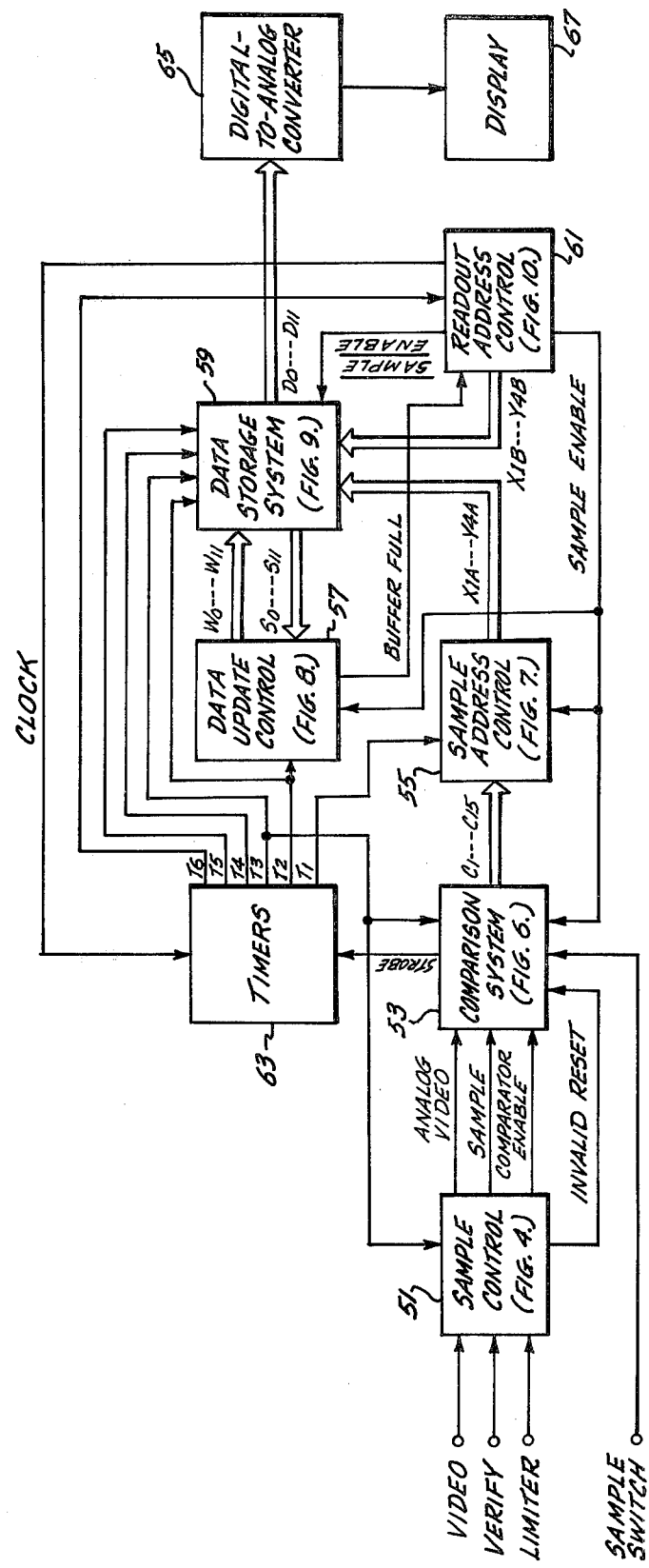
FIG. 3 is a block diagram of an electronic subsystem of a particle size analyze formed in accordance with the invention for analyzing the output of a laser anemometer and providing a histogram of particle number versus size.

FIG. 3 is a block diagram of an electronic subsystem suitable for use in a particle size analyzer formed in accordance with the invention and comprises: a sample control 51; a comparison system 53; a sample address control 55; a data update control 57; a data storage system 59; a readout address control 61; timers 63; a digital-to-analog converter 65; and, a display 67. FIGS. 4 and 6-10 are block diagrams that illustrate in detail the major subsystems illustrated in FIG. 3. Prior to describing these subsystems, a brief description of the nature and operation of the electronic subsystem illustrated in FIG. 3 is set forth.

The sample control 51 receives the VIDEO, VERIFY and LIMITER signals produced by the crossed beam laser anemometer. The VIDEO signal is buffered and applied to the comparison system 53 (ANALOG VIDEO signal). The LIMITER signal is analyzed to determine whether or not an adequate number of fringes have been intersected by the particle producing the VIDEO signal. The adequacy of the number of fringes is manually adjustable and may be set to 10, 15, etc. fringes, as desired. An adequate number of fringes must be intersected, and a VERIFY signal must be received, in order for the sample control to produce outputs that allow the ANALOG VIDEO signal applied to the comparison system 53 to be measured. In this regard, as will be better understood from the following discussion of a preferred embodiment of the sample control illustrated in FIG. 4, the sample control 51 produces a COMPARATOR ENABLE signal that enables the comparison system 53 upon the receipt of the first wave of the LIMITER signal. Thereafter a SAMPLE signal is produed if an adequate number of fringes have been crossed by the particle and a VERIFY signal has been received. If these required conditions are not met, an INVALID RESET signal resets the comparison system. The production of a SAMPLE signal (pulse) allows an ANALOG VIDEO signal measurement made by the comparison system to be forwarded to the sample address control, as an address signal, as discussed below.

As discussed above, the number of fringes crossed determines how close the particle is to the center of the probe. When a small number of fringes are crossed, the particles is located near the edges of the probe, and when a large number are crossed, the particle is near the center. By controlling the number of fringes that need to be crossed, in order for a signal to be considered valid, control over the portion of the probe through which particles must pass in order to be measured is provided.

The comparison system 53 compares the ANALOG VIDEO signal with a variable reference voltage. More specifically, the comparison system includes a plurality of step related comparators that produce a parallel digital data signal whose nature is related to the magnitude of the ANALOG VIDEO signal. The parallel digital data signal (denoted C1-C15) is applied to the sample address control 55. The sample address control produces an X-Y address whose nature is determined by the nature of the C1-C15 signal. The X-Y address is applied to the address input of the data storage system 59. Thus, the address applied to the data storage system is determined by the magnitude of the ANALOG VIDEO signal.

In accordance with the X-Y address produced by the sample address control 55, the data storage system produces a bin data signal on its output (denoted S0-S11), which is applied to the data update control 57. The data update control 57, thereafter, updates the bin data signal by one. The bin data signal is then written back into the same bin in the data storage system 59. The timing of these operations is controlled by certain outputs (denoted T1-T3) of a portion of the timers 63. Outputs (denoted T4-T6) of another portion of the timers 63 control the data storage system 59 and the readout address control 61 during the readout mode of operation. In this regard, when any of the bins of the data storage system become full, the readout address control 61 is automatically actuated by a BUFFER FULL signal. Actuation of the readout address control 61 causes a series of X-Y readout address signals (denoted X1B-Y4B) to be applied to the data storage system 59. The readout address signals cause the bins of the data storage system 59 to be sequentially addressed. As the data storage system bins are sequentially addressed, the data stored therein (denoted D0-D11) is transmitted to the digital-to-analog (D/A) converter 65. The D/A converter converts the digital data to analog data, which is applied to the display 67.

In summary, the magnitude of the VIDEO signal (which is related to the intensity of the scattered light blinked on and off by a particle) controls the addressing of the data storage system. Each time a particular intensity signal occurs, the count value stored in an intensity related bin is updated. Since intensity is related to size, the bin counts are related to the number of particles of a particular size that have been analyzed. When a bin is full, the stored data is automatically read out. Alternatively, if desired, the data stored in the bins can be read out at predetermined time intervals.

Figure 4:
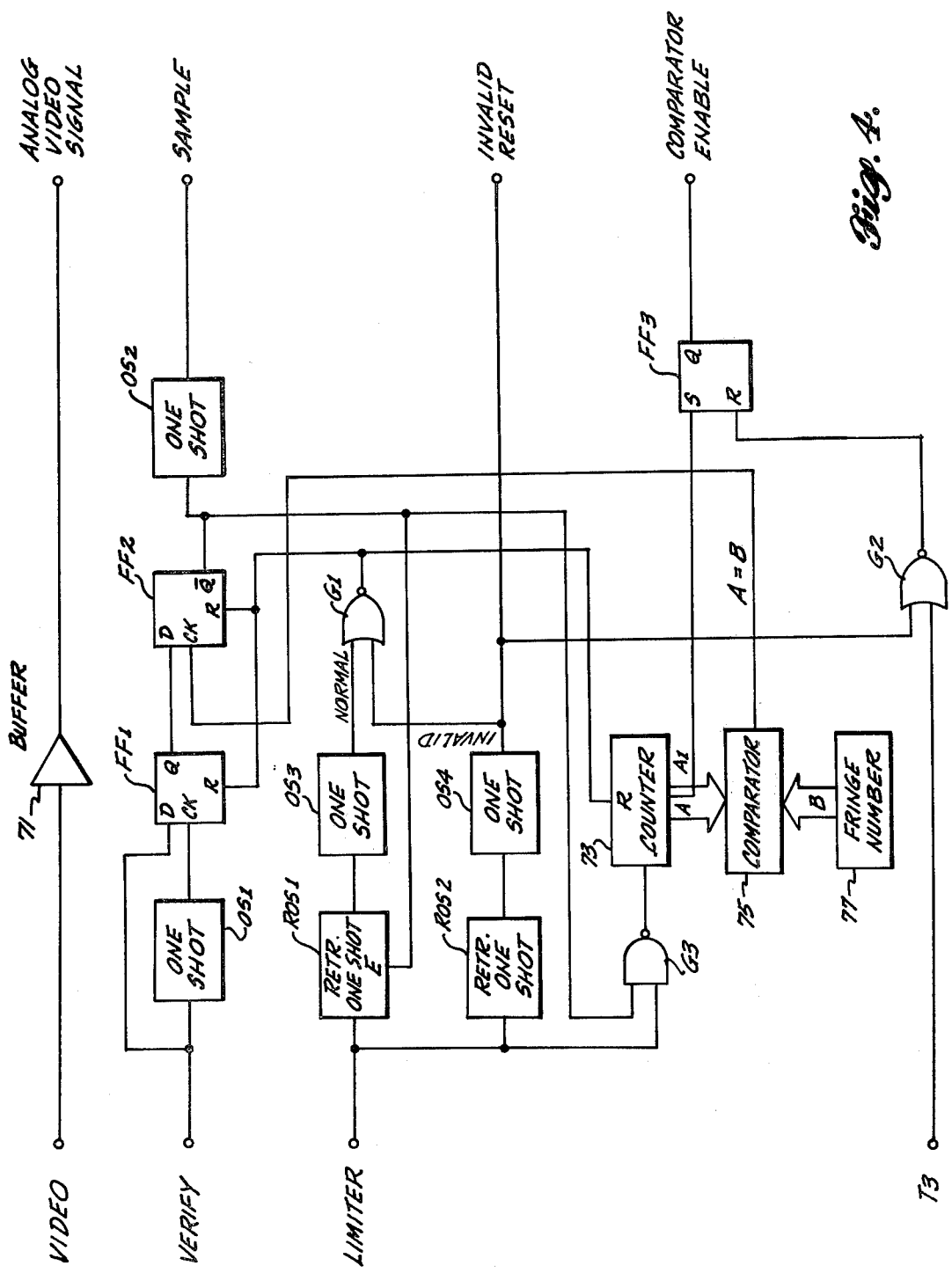
FIG. 4 is a block diagram of a sample control suitable for use in the electronic subsystem illustrated in FIG. 3.

FIG. 4 is a block diagram of a sample control suitable for use in the particle size analyzer illustrated in FIG. 3 and comprises: a buffer amplifier 71; four one-shot multivibrators designated OS1, OS2, OS3 and OS4; two retriggerable one-shot multivibrators designated ROS1 and ROS2 (ROS1 has an externally controlled enable input); two D flip-flops designated FF1 and FF2; an SR (set/reset) flip-flop designated FF3; two two-input NOR gates designated G1 and G2; a two-input NAND gate designated G3; a counter 73; a comparator 75; and a fringe number control 77.

As will be better understood from the following description of FIG. 4 and the other subsystems illustrated in FIGS. 6–10, only the functional inputs of the illustrated logic is described here. Nonfunctional inputs are tied to a suitable voltage level (or ground) such that the each logic item functions in the described manner. For example, the set inputs of neither FF1 nor FF2 are described, because they are not controlled. Similarly, only the functional outputs of the illustrated logic are described. Unused outputs (with respect to the described invention) are neither illustrated nor described.

The VIDEO signal produced by the crossed beam laser anemometer is applied to the input of the buffer amplifier 71. The output of the buffer amplifier 71 is the ANALOG VIDEO signal applied to the comparison system, illustrated in FIG. 3 and hereinafter described in more detail with respect to FIG. 6. The VERIFY signal, which is a pulse produced by the laser anemometer, is applied to the trigger input of OS1 and the D input of FF1. The output of OS1 is connected to the clock (CK) input of FF1. The Q output of FF1 is connected to the D input of FF2. The $\bar{Q}$ output of FF2 is connected to the trigger input of OS2. The output of OS2 is the SAMPLE signal applied to the comparison system 53.

The LIMITER signal, which is a square wave produced by the laser anemometer, is applied to the trigger inputs of ROS1 and ROS2 and to one input of G3. The output of ROS1 is connected to the trigger input of OS3 and the output of OS3 (which is designated NORMAL to denote normal reset) is applied to one input of G1. The output of ROS2 is connected to the trigger input of OS4 and the output of OS4 (which is designated INVALID to denote an invalid reset) is applied to the second input of G1 and to the comparison system. This signal is the INVALID RESET signal noted above and hereinafter described in more detail. The output of G1 is applied to the reset inputs of FF1 and FF2 and to the reset input of the counter 73.

In addition to being applied to the input of OS2, the $\bar{Q}$ output of FF2 is also applied to the enable input of ROS1 and to the second input of G3. The output of G3 is applied to the count input of the counter 73. The counter 73 produces a parallel digital output, denoted A, which is applied to one input of the comparator 75. The fringe number control 77 produces a fringe value in parallel digital form, designated B, which is applied to the second input of the comparator 75. When A and B are equal, the A=B output of the comparator 75 shifts from low to high, which shift is applied to the clock input of FF2. Further, the A1 (least significant bit) output of the counter 73 is applied to the set(S) input of FF3. Since A1 is the LSB output of the counter 73, A1 shifts from low to high when the first limiter square wave occurs. The output of OS4 (INVALID RESET) is applied to one input of G2 and a timing signal, produced by the timers 63 (FIG. 3) and denoted T3, is applied to the second input of G2. The output of G2 is applied to the reset (R) input of FF3. The $\bar{Q}$ output of FF3 is the COMPARATOR ENABLE signal applied to the comparison system 53.

Figure 5B:
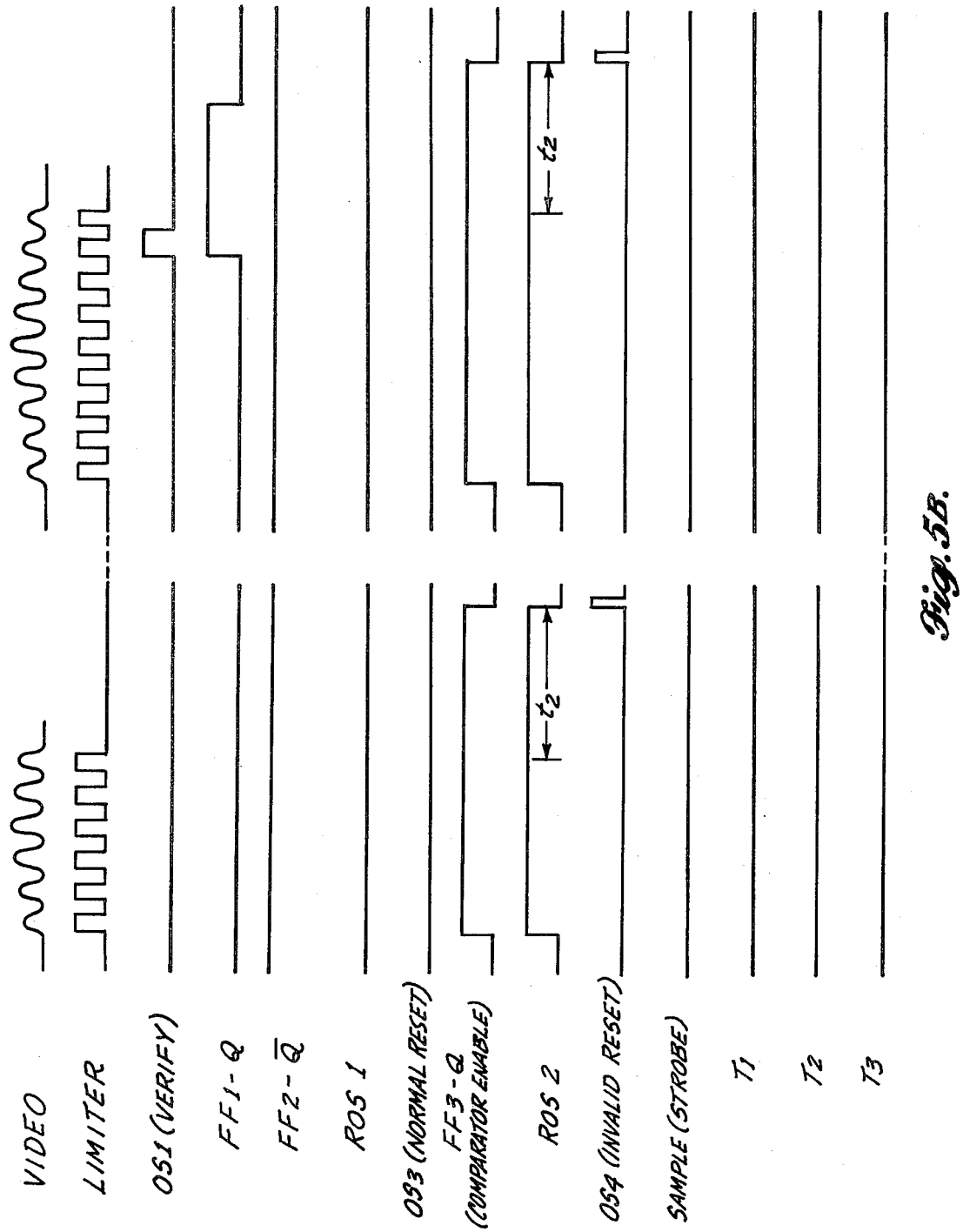

FIGS. 5A and 5B are timing diagrams illustrating the three different sequences of operation of the sample control 51 illustrated in FIG. 4. Which of these three different sequences occurs depends upon the nature of the VIDEO signal. The first sequence is illustrated in FIG. 5A and occurs when a valid VIDEO signal is received. Valid means that the VIDEO signal is verified by the laser anemometer as being produced by a single particle passing through a minimal number of fringes and verified by the invention as passing through the number of fringes determined by the setting of the fringe number control 77. The second sequence is illustrated on the left of FIG. 5B and occurs when the VIDEO signal is determined to be invalid by the laser anemometer. In this situation no VERIFY pulse occurs. The third sequence is illustrated on the right of FIG. 5B. In this sequence a VERIFY pulse occurs, however, the VIDEO signal is determined to be invalid by the invention because an inadequate number of fringes are traversed by the particle, i.e., the number of fringes is less than the number determined by the setting of the fringe number control.

Turning first to a discussion of the operation of the sample control 51 when a valid VIDEO signal is produced. As previously indicated, the sequence covering this situation is illustrated in FIG. 5A. For purposes of discussion, the illustrated VIDEO signal is produced by scattered light that alternately blinks on and off twenty one (21) times, i.e., the particle passes through twenty one fringes. This VIDEO signal is illustrated on the first line of FIG. 5A. Located on the next line is the LIMITER signal produced by the laser anemometer in response to the VIDEO signal. As previously discussed, the LIMITER signal is a square wave signal having a frequency equal to the frequency of the VIDEO signal. More precisely, the LIMITER signal is a square wave signal that "tracks" the VIDEO signal.

Assuming that the laser anemometer analyzes the first eight cycles of the VIDEO signal to determine whether or not the VIDEO signal is a valid (i.e., produced by a single particle), when the eighth LIMITER signal wave occurs, a VERIFY pulse is produced. The VERIFY pulse triggers OS1. Since a VERIFY pulse is present when OS1 is triggered, FF1 is set. Consequently, the Q output of FF1 shifts from low to high, whereby a high is present on the D input of FF2. This high, however, is not immediately clocked into FF2. Rather, FF2 is not clocked until the comparator determines that an adequate number of LIMITER waves have occurred. More specifically, prior to the high on the output of FF1 being clocked into FF2, the $\bar{Q}$ output of FF2 is high. As a result, G3 is enabled. Consequently, the square waves forming the LIMITER signal are applied to the counter 73. The counter counts up each time a LIMITER wave occurs. When the parallel output of the counter 73 (A) reaches a magnitude that compares with the parallel output (B) of the fringe number control 77, the A=B output of the comparator 75 shifts from low to high. For example, the fringe number counter 77 may be manually set to produce a parallel output equal to the decimal number 10, 15 etc. Assuming it is set to 10, when 10 square waves are counted by the counter 73, the A=B output of the comparator 75 shifts from low to high. This shift clocks the output of FF1 into FF2. As a result, the $\overline{Q}$ output of FF2 shifts rom high to low, which action enables OS2 to be triggered. OS2 is not yet triggered because OS2 is triggered on a low to high shift not a high to low shift. This sift occurs when FF2 is reset as hereinafter described. (It is pointed out here that the one-shots and the retriggerable one-shots can be fired on either a low to high shift or a high to low shift, depending upon how they are physically wired, as will be readily understood by those skilled in the art. Thus, the descriptive firing statements herein set forth should be taken as exemplary, not limiting.)

When FF2 is clocked, and its $\overline{Q}$ output shifts from high to low, G3 is immediately disabled. As a result, the counter 73 does not receive any further LIMITER signal square waves. Further, when the $\overline{Q}$ output of FF2 shifts from high to low, ROS1 is enabled. As a result, the output of ROS1 shifts from low to high, upon the occurrence of the next LIMITER signal square wave. (Prior LIMITER signal square waves did not, of course, trigger ROS1, because it was disabled.) Each subsequent LIMITER signal square wave "retriggers" ROS1. Since OS3 is triggered when the output of ROS1 shifts from high to low, as long as ROS4 continues to be triggered, no pulse is produced by OS3. Contrariwise, a predetermined time period ($t_1$) after the end of the last LIMITER signal square wave, the output of ROS1 shifts from high to low. (See line 6, FIG. 5A). As a result, OS3 is fired. The firing of OS3 creates the NORMAL reset pulse. The NORMAL reset pulse resets FF1, FF2 and the counter 73, and the sample control is reset and made ready to receive the next VIDEO signal. Resetting of FF2 causes OS2 to be triggered, as previously described, whereby a SAMPLE pulse is applied to the comparison system.

While a INVALID reset pulse does occur during this sequence, the INVALID reset pulse does not have any effect, because FF1, FF2, and the counter 73 have already been reset by a NORMAL reset pulse. More specifically, the INVALID reset pulse has no effect when a valid VIDEO signal is received because the period of time between the termination of the last LIMITER signal square wave and the shifting of the output of ROS2 from high to low, i.e., the time out period of ROS2 ($t_2$), is greater than the time out period ($t_1$) of ROS1.

When the counter 73 counted the first LIMITER pulse square wave, A1 shifted states. This shift set FF3, whereby the COMPARATOR ENABLE signal shifted from low to high. FF3 remains set until a T3 pulse occurs. As will be better understood from the following discussion of the preferred embodiment of the comparison system 53 illustrated in FIG. 6, T3 occurs a predetermined time period after a SAMPLE pulse is produced as a result of OS2 being fired. (This time period is adequate for the C1-C15 output of the comparison system to be used to update the related bin of the data storage system 59.)

The sequence illustrated in timing diagram on the left side of FIG. 5B, is for a VIDEO signal produced by a particle that passes through only six fringes. As a result, only six LIMITER signal squares are produced. Since the laser anemometer needs at least eight waves to produce a VERIFY pulse, none occurs. As a result OS1 is not fired and the Q output of FF1 remains low. Thus, the $\overline{Q}$ output of FF2 remains high. This output remains high both because the Q output of FF1 remains low and because the counter 73 does not count enough LIMITER signal waves for its A=B output to shift high. Because the $\overline{Q}$ output of FF2 remains high, ROS1 is not enabled, whereby the output of ROS1 remains low. Consequently, OS3 is not triggered and a NORMAL reset pulse does not occur. Rather, as shown on line 9, $t_2$ after the last LIMITER signal square wave occurs, the output of ROS2 shifts low, whereby OS4 is fired and an INVALID RESET pulse occurs. The INVALID reset pulse resets the counter 73. The INVALID RESET pulse also resets FF3 via G2, whereby the COMPARATOR ENABLE signal, which shifted from low to high upon the occurrence of the first LIMITER signal square wave returns to its low state. Finally, the INVALID RESET pulse resets the comparison system in the manner hereinafter described. As will be better understood from the following description, since OS2 is not triggered, whereby a SAMPLE pulse does not occur, the T1, T2 and T3 data bin updating pulses do not occur.

The VIDEO signal of the sequence illustrated on the right side of FIG. 5B causes nine LIMITER signal square waves to be produced. As a result, assuming the waves are produced as the result of a single particle passing through nine fringes, after analysis, the laser anemometer produces a VERIFY pulse. The VERIFY pulse fires OS1 and, thus, is clocked into FF1, whereby the Q output of FF1 shifts from low to high. However, a SAMPLE pulse is not produced, because the high output of FF1 is never clocked into FF2 and FF2 reset. Rather, since only nine LIMITER signal square waves are produced, the A=B output of the comparator 75 remains low (assuming B is set to equal ten). Since the A=B output remains low, FF2 is not clocked, whereby the $\overline{Q}$ output of FF2 remains high. Since the $\overline{Q}$ output of FF2 remains high, ROS1 remains disabled. After the nine LIMITER signal square waves have triggered and then retriggered ROS2 and the time-out period of ROS2 ($t_2$) runs out, OS4 is fired and an INVALID RESET pulse is produced. The INVALID RESET pulse, via G1 resets FF1 and the counter 73. The INVALID RESET pulse also resets FF3, which was set when the first LIMITER signal square wave was counted by the counter 73. Further, the INVALID RESET pulse resets the comparison system, as hereinafter described in more detail. Finally, since no SAMPLE pulse is produced, no T1, T2 or T3 pulses occur.

Figure 6:
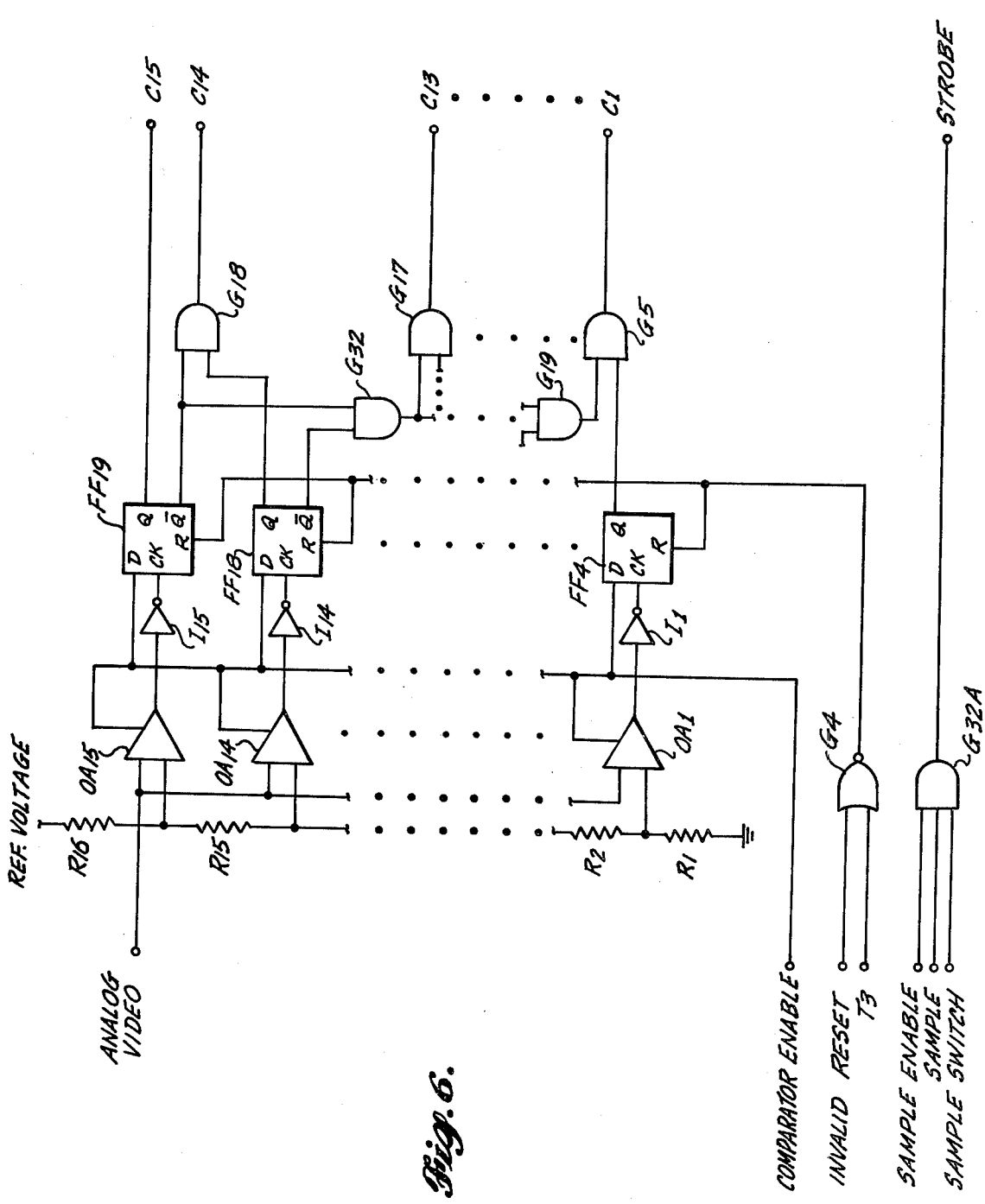
FIG. 6 is a block diagram of a comparison system suitable for use in the electronic subsystem illustrated in FIG. 3.

FIG. 6 is a block diagram of a comparison system suitable for use in the particle size analyzer illustrated in FIG. 3 and comprises: fifteen operational amplifiers designated OA1-OA15; fifteen inverters designated I1-I15; fifteen D flip-flops designated FF4-FF19; a two-input NOR gate designated G4; twenty seven two-input AND gates designated G5-G32 (comprising fourteen output gates G5-18 and thirteen control gates G19-G32); a three-input AND gate designated G32A;

and, sixteen resistors designated R1–R16. As will be understood from viewing FIG. 6 and the following discussion, the comparison system is, in essence, a fifteen "channel" comparator. Since the channels are substantially identical, for ease of illustration, only selected ones of the resistors, operational amplifiers, inverters, flip-flops and two-input AND gates are illustrated in FIG. 6. The non-illustrated resistors, operational amplifiers, inverters, flip-flops and two-input AND gates are connected in a manner similar to the connections connecting the illustrated elements together in FIG. 6, as will be readily appreciated by those familiar with digital logic design from viewing FIG. 6 and reading the following discussion.

The ANALOG VIDEO signal output of the sample control 51 (FIG. 3) is connected to one of the same inputs (either inverting or noninverting, as dictated by the specific nature of the operational amplifiers and the polarity of the reference voltage source) of each of the operational amplifiers OA1–OA15 (FIG. 6). The other inputs (noninverting or inverting) are connected to the junctions of a voltage divider formed by R1–R16. More specifically, R1–R16 are connected in series in numerical order between ground and a reference voltage source. The junction between R1 and R2 is connected to the appropriate input of OA1; the junction between R2 and R3 is connected to the appropriate input of OA2; etc., with the last connection connecting the junction between R15 and R16 to the appropriate input of OA15. As will be readily appreciated from the foregoing description, the operational amplifiers from a series of comparators. Each comparator, in numerical ascending order, compares the ANALOG VIDEO signal with a higher voltage level comparison signal. The incremental division between comparison steps is determined by the value of the individual resistors. In this regard, preferably, the resistance values of R1–R15 are the same, whereby, the comparison steps are the same.

The COMPARATOR ENABLE signal produced by FF3 of the sample control 51 is applied to the enable inputs of each of OA1-OA15; and, to the D inputs of each of FF4-FF19. The output of OA1 is connected through I1 to the clock (CK) input of FF4; the output of OA2 is connected through I2 to the clock input of FF5; etc., with the last such connection being the output of OA15 connected through I15 to the clock input of FF19.

The INVALID RESET signal produced by the sample control 51 is applied to one input of G4. T3 is applied to the second input of G4. The output of G4 is connected to the reset inputs of FF4-FF19. The $\overline{Q}$ output of FF19 is applied to one input of G18 and to one input of G32. The Q output of FF18 is applied to the second input of G18. The $\overline{Q}$ output of FF18 is applied to the second input of G32. The output of G32 is applied to one input of G17. This arrangement is continued, with the last connection being such that the Q output of FF4 is connected to one input of G5; and the output of G19 is connected to the second input of G5. The outputs of G5-G18, and the Q output of FF19 form the parallel digital data signal designated C1-C15, generally discussed above with respect to FIG. 3.

As noted above G5-G18 are output gates and G19-G32 are control gates. In combination these gates form a decoder that decodes the outputs of FF4-FF19 such that only one of C1-C15 is high at any one time. Which one of C1-C15 is high is related to the highest one of F4-F19 that is set. That is, as will be better understood from the following discussion, the magnitude of the highest fluctuation of the ANALOG VIDEO signal determines which ones of FF4-FF19 are set. In this regard all of FF4-FF19 at and below the highest fluctuation of the ANALOG VIDEO signal are set. The AND gate decoder (G5-G32) decodes the FF4-FF19 states such that one and only one of C1-C15 is high. For example, if all of F4-F19 are set, C15 will be high, all others (C1-C14) will be low because G32 (and thus all of the control gates) will be disabled. Since all of the control gates are disabled, all lower output gates (G5-G17) will be disabled. G18 will not produce a high output because one of its inputs (the $\overline{Q}$ output of FF19) will be low. As a second example, if only F4-F18 are set G18 will be enabled by the $\overline{Q}$ output of FF19. Since the Q output of FF18 will be high C14 will be high. C15 and C1-C13 will be low. C15 will be low because the Q output of FF19 is low. C1-C13 will be low because the output of G32 will be low, whereby all lower order output gates (G5-G17) will be disabled. In a similar manner the C output related to the highest one of the other flip-flops that is set will be the only output that is high.

As noted above, T3 is applied to the second input of G4. T3 resets FF4-FF19 when a valid VIDEO signal has been received, after the C1-C15 signal is read, as will be better understood from the following discussion of the subsystems illustrated in FIGS. 7–9. Alternatively, if the C1-C15 signal is not to be read an INVALID RESET pulse, produced in the manner previously described, resets FF4-FF19. Thus, either an INVALID RESET or a T3 pulse resets FF4-FF19.

A signal denoted SAMPLE ENABLE, produced by the read-out address control 61 in the manner hereinafter described, is applied to one input of G32A. The SAMPLE pulse produced by OS2 of the sample control 51 in the manner previously described is applied to the second input of G32A. The third input of G32A is connected to a sample control switch. When the sample control switch is in an appropriate position, it applies an enable signal to the third input of G32A. The output of G32A is a signal denoted STROBE that is applied to the timers 63 (FIG. 3).

In operation, when COMPARATOR ENABLE shifts high, which happens when the first LIMITER signal square wave occurs, as previously described, OA1-OA15 are enabled. The enabled operational amplifiers, which form high speed voltage comparators, compare the fluctuations of the ANALOG VIDEO signal with their respective reference voltages. Depending upon the magnitude of the highest fluctuation, one or more of the operational amplifier outputs shift from high to low. Thus, the outputs of all of the operational amplifiers including the one at or immediately below the magnitude of the highest fluctuation of the ANALOG VIDEO signal shift from high to low. The negative going outputs of these operational amplifier comparators are inverted by I1-I15. The inverted signals clock the corresponding of D flip-flops. While date provided by COMPARATOR ENABLE, which is high, is presented to all of F4-F19, only those flip-flops that are clocked, clock this data in. As a result, only the $\overline{Q}$ outputs of the clocked flip-flops shift from high to low and only the Q outputs shift from low to high. (Later lower fluctuations will not disturb higher fluctuation settings because the higher order flip-flops are not clocked.) The other (unclocked) flip-flops remain in their reset state. The inverters I1-I15 are included to prevent oscillation of any operational amplified that receives an ANALOG VIDEO signal near its threshold level without having to apply hysteresis, which would not be useful in the present system. The outputs of FF4-FF19 are decoded by a decoding network formed of the two-input AND gates, as previously described.

A STROBE pulse occurs each time a SAMPLE pulse occurs, if the sample switch is in the appropriate position and SAMPLE ENABLE, which is produced by the readout address control in the manner hereinafter described, is high. In other words, when these conditions are met, STROBE pulses track SAMPLE pulses. The STROBE pulse is applied to the timers 63 and causes a T1, T2 and T3 sequence to occur, as illustrated in FIG. 5A. If an INVALID RESET pulse occurs, FF4-FF19 are immediately reset. Alternatively, after the sample cycle is complete and the decoded FF4-FF19 outputs readout, when a T3 pulse occurs, FF4-FF19 are reset.

Figure 7:
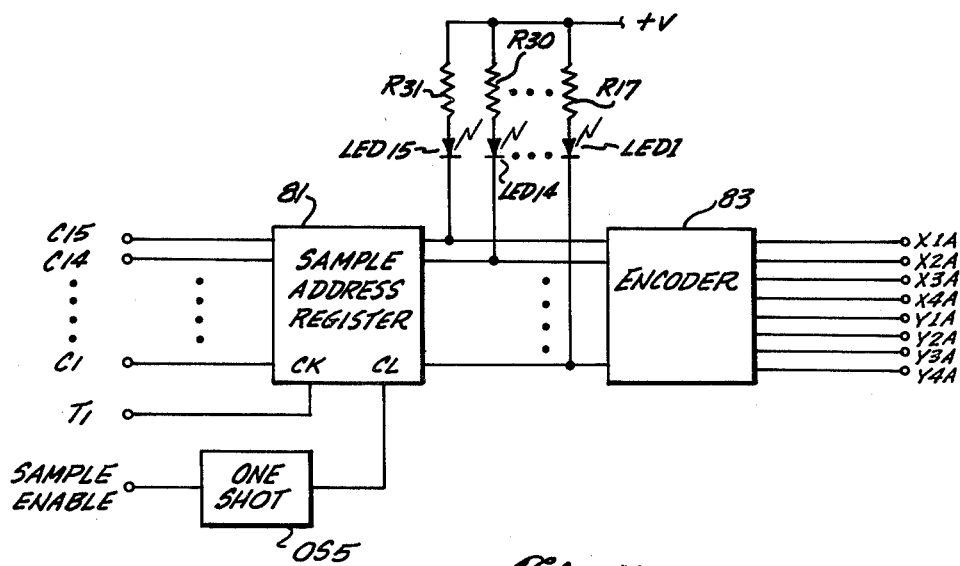
FIG. 7 is a block diagram of a sample address control suitable for use in the electronic subsystem illustrated in FIG. 3.

FIG. 7 is a block diagram of a sample address control suitable for use in the electronic subsystem illustrated in FIG. 3 and comprises: a sample address register 81; an encoder 83; fifteen resistors designated R17-R31; fifteen light emitting diodes designated LED1-LED15; and, a one-shot multivibrator designated OS5. C1-C15 are applied to parallel inputs of the sample address register 81. The sample address register reads its parallel inputs when it receives a clock pulse, denoted T1 and produced by the timer 63 as hereinafter described, at its clock (CK) input.

A SAMPLE ENABLE signal produced by readout address control 61 in the manner hereinafter described is applied to the trigger input of OS5. The output of OS5 is applied to the clear (CL) input of the sample address register 81. As will be better understood from the following discussion of the readout address control illustrated in FIG. 10, SAMPLE ENABLE is normally high. At the start of the readout mode of operation, SAMPLE ENABLE shifts low. This high to low shift triggers OS5 whereby a pulse is applied to the sample address register. As a result the sample address resister is cleared. Contrariwise, during the sample mode of operation, the sample address register reads its input and changes its output in accordance therewith each time it is clocked by a T1 pulse.

The sample address register produces fifteen parallel outputs that are applied to fifteen inputs of the encoder 83. In addition, each output of the sample address register 81 is applied to the cathode of a related one of LED1-LED15. The anodes of LED1-LED15 are connected to a voltage source designated +V via R17-R31, respectively.

The encoder 83 produces X-Y address signals denoted X1A, X2A, X3A, X4A, Y1A, Y2A, Y3A and Y4A. The binary state (e.g., high or low) of the address signals are related to the binary state of the signals received from the sample address register S1. Thus, the X-Y address is related to the nature of the C1-C15 signal. Since only one line of the C1-C15 parallel signal is high, and all the rest are low, the high signal line, in essence, controls the X-Y address produced by the encoder 83.

In operation, as will be understood from viewing line 12 of FIG. 5A, T1 occurs immediately subsequent to the occurrence of a STROBE pulse. As a result, the sample address register 81 is clocked immediately after a valid VIDEO signal ends, which is subsequent to the time that FF4-FF19 of the comparison system 53 are clocked by the ANALOG VIDEO signal. Thus, the sample address register 81 reads and stores the output of the comparison system related to the magnitude of the highest fluctuation of a valid VIDEO signal. The encoder 83 reads the C1-C15 data stored in the sample address register 81 and, in accordance therewith, produces a related X-Y address signal. The nature of the X-Y address signal, i.e., the address, is defined by the high/low values of X1A-X4A and Y1A-Y4A. The on-/off state of LED1-LED15 denote the contents of the sample address register and, thus, the magnitude of the received VIDEO signal. As a result, the LED1-LED15 data can be used to provide an instantaneous real time display of detected particle size, if desired.

Figure 8:
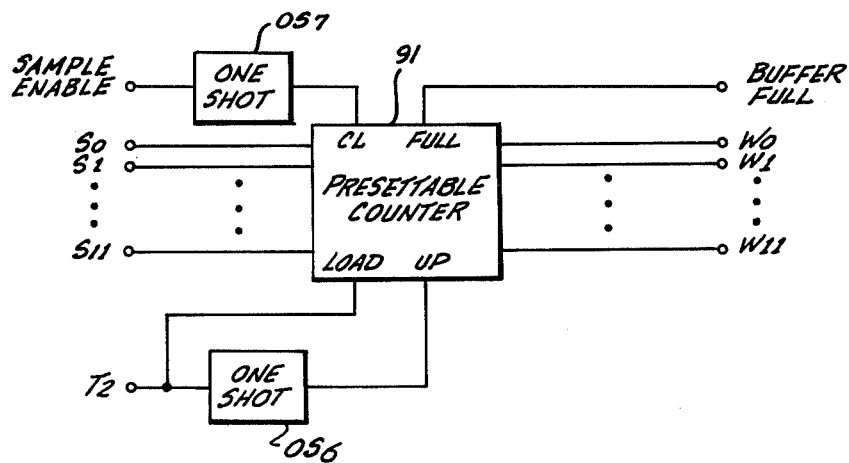
FIG. 8 is a block diagram of a data update control suitable for use in the electronic subsystem illustrated in FIG. 3.

FIG. 8 is a block diagram of a data update control 57 (FIG. 3) suitable for use in the electronic subsystem illustrated in FIG. 3 and comprises a presettable counter 91; and, two one-shot multivibrators designated OS6 and OS7. The preset inputs of the presettable counter are connected to receive or read data (S0-S11) present on the outputs of the data storage system 59 (FIG. 3). This data is located in the data bin at the address of the X-Y address signal produced by the encoder 83, as hereinafter discussed in more detail with respect to the data storage system 59 illustrated in FIG. 9. The S0-S11 data is read when a T2 pulse, produced by the timer 63, is applied to the load input of the presettable counter.

The T2 pulse is also applied to the input of OS6. The output of OS6 is applied to the UP input of the presettable counter 91. As illustrated on the thirteenth line of FIG. 5A, a T2 pulse occurs subsequent to the occurrence of a T1 pulse, in timed relationship thereto. Since the T1 pulse occurs prior to the T2 pulse, the desired X-Y address occurs on the output of the encoder prior to a T2 pulse causing the data at that address to be loaded into the presettable counter. The S0-S11 data is loaded at the leading edge of the T2 pulse. OS6 is triggered at the trailing edge of the T2 pulse; and, the pulse produced by OS6 when it is triggered causes the presettable counter to be incremented by one. Thus, the presettable counter is incremented by one after it is loaded with a count value at the X-Y address determined by the size of the particle whose light created the VIDEO signal that was analyzed.

The output of the presettable counter, which is denoted W0-W11, is then written back into the same data storage bin of the data storage system. Thus, the W0-W11 data is the S0-S11 data incremented by one. In this way bin data (which is related to particle size) is updated each time a particle of the size related to a particular bin data is detected. When the presettable counter is incremented to a full state during an updating sequence, it produces an output signal denoted BUFFER FULL. BUFFER FULL is applied to the readout address control 61 and causes the particle size analyzer to shift from a sample mode of operation to a readout mode of operation. During the readout mode of operation SAMPLE ENABLE, which is applied to OS7, causes OS7 to fire. The output of OS7 is connected to the clear (CL) input of the presettable counter. More specifically, SAMPLE ENABLE shifts from high to low at the start of the readout sequence. This shift causes OS7 to fire, whereby the presettable counter 91 is cleared.

Figure 9:
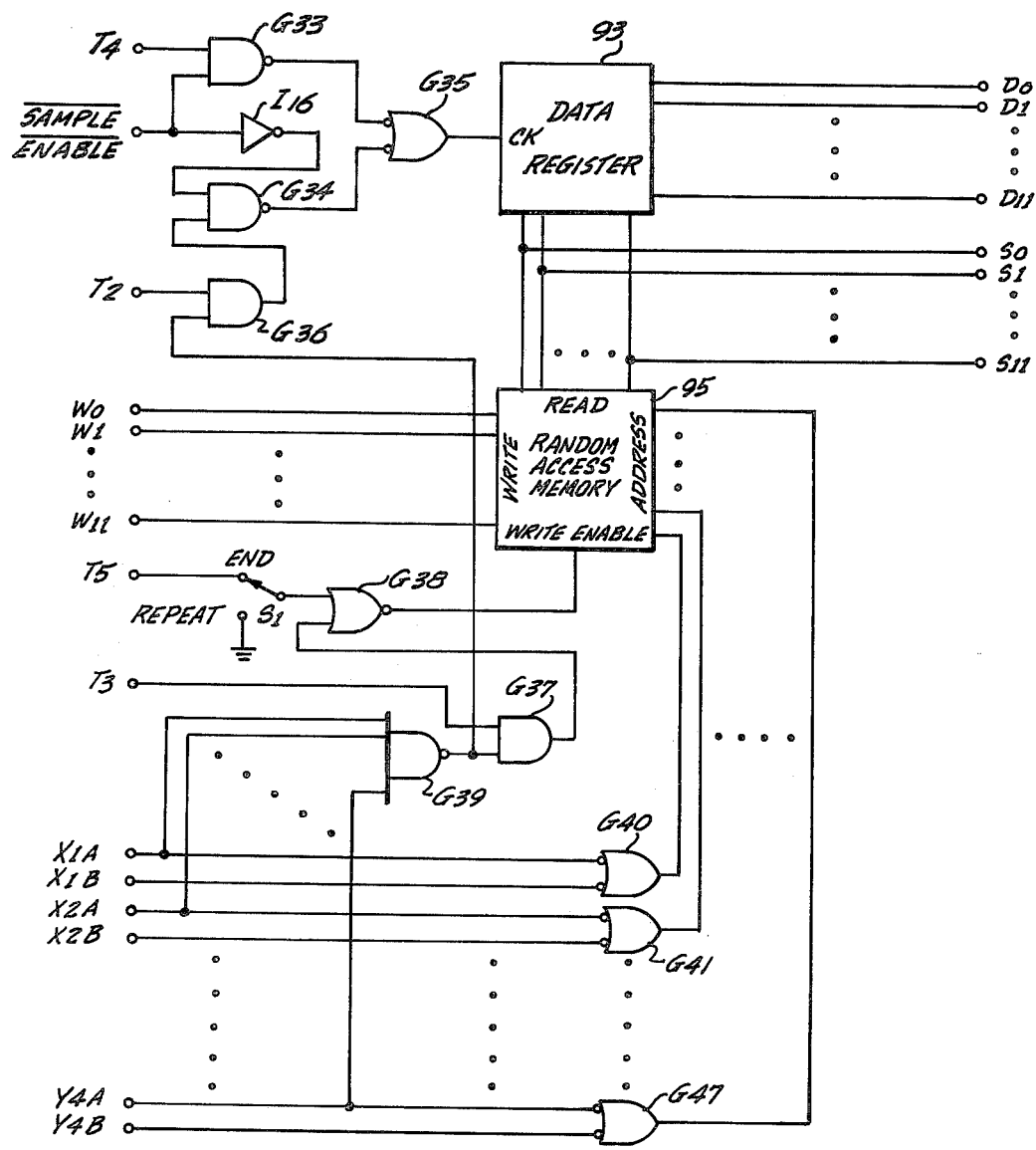
FIG. 9 is a block diagram of a data storage system suitable for use in the electronic subsystem illustrated in FIG. 3.

FIG. 9 is a block diagram of a data storage system suitable for use in the electronic subsystem illustrated in FIG. 3 and comprises: a data register 93; a random access memory (RAM) 95; an inverter designated I16; two two-input NAND gates designated G33 and G34; a two-input negative OR gate designated G35; two two-input AND gates designated G36 and G37; a two-input NOR gate designated G38; an eight-input NAND gate designated G39 (or, more exactly, a series of gates suitably connected to form an eight-input NAND gate); and, eight two-input negative OR gates designated G40-G47.

Figure 11:
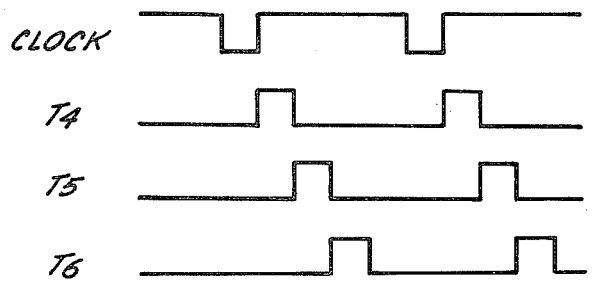

A timing signal, denoted T4 and produced by the timer, is applied to one input of G33. As illustrated in FIG. 11, T4 occurs immediately subsequent to the occurrence of a clock pulse produced by the readout address control 61 in the manner hereinafter described. A signal denoted $\overline{\text{SAMPLE ENABLE}}$, which is the complement of SAMPLE ENABLE, and is also produced by the readout address control, is applied to the second input of G33. $\overline{\text{SAMPLE ENABLE}}$ is also applied through I16 to one input of G34. T2 is applied to one input of G36. The output of G36 is connected to the second input of G34. The outputs of G33 and G34 are each connected to one input of G35. The output of G35 is connected to the clock (CK) input of the data register 93. The data input of the data register 93 is connected to the read output of the RAM 95. More specifically, the S0-S11 data signal occurs on the read output of the RAM 95. In addition to S0-S11 being applied to the presettable counter 91 (FIG. 8), the S0-S11 data signal is also applied to the data input of the data register 93. The output of the data register 93 is the parallel data signal designated D0-D11.

As will be readily appreciated by those skilled in the art, when a pulse occurs on the output of G35, the data register reads the S0-S11 data present on the read output of the RAM 95. This signal is then reflected in the D0-D11 output of the data register 93. Thereafter, the D0-D11 data remains the same, even though the S0-S11 signal changes, until the data register is again clocked by a pulse occurring on the output of G35.

A timing pulse denoted T5, also produced by the timer 63, is applied to one remote terminal (denoted END) of a switch designated S1. T5, as illustrated in FIG. 11, occurs immediately subsequent to the occurrence of a T4 pulse. The other remote terminal of S1, denoted REPEAT, is connected to ground. The common terminal of S1 is connected to one input of G38. The output of G38 is connected to the write enable input of the RAM 95. The write input of the RAM 95 receives the W0-W11 signal produced by the presettable counter 91 in the manner heretofore described.

A T3 pulse is applied to one input of G37. X1A, X2A, X3A, X4A, Y1A, Y2A, Y3A and Y4A are each applied to one of the eight inputs of G39. The output of G39 is connected to the second input of G36 and to the second input of G37. The output of G37 is connected to the second input of G38. X1A and X1B are each connected to one input of G40; X2A and X2B are each connected to one input of G41. In a similar manner, X3A, X3B; X4A, X4B; Y1A, Y1B; Y2A, Y2B; Y3A, Y3B; and Y4A, Y4B are each connected to one input of G42-G47, respectively. The outputs of G40-G47 are connected to the address inputs of the RAM 95.

Figure 10:
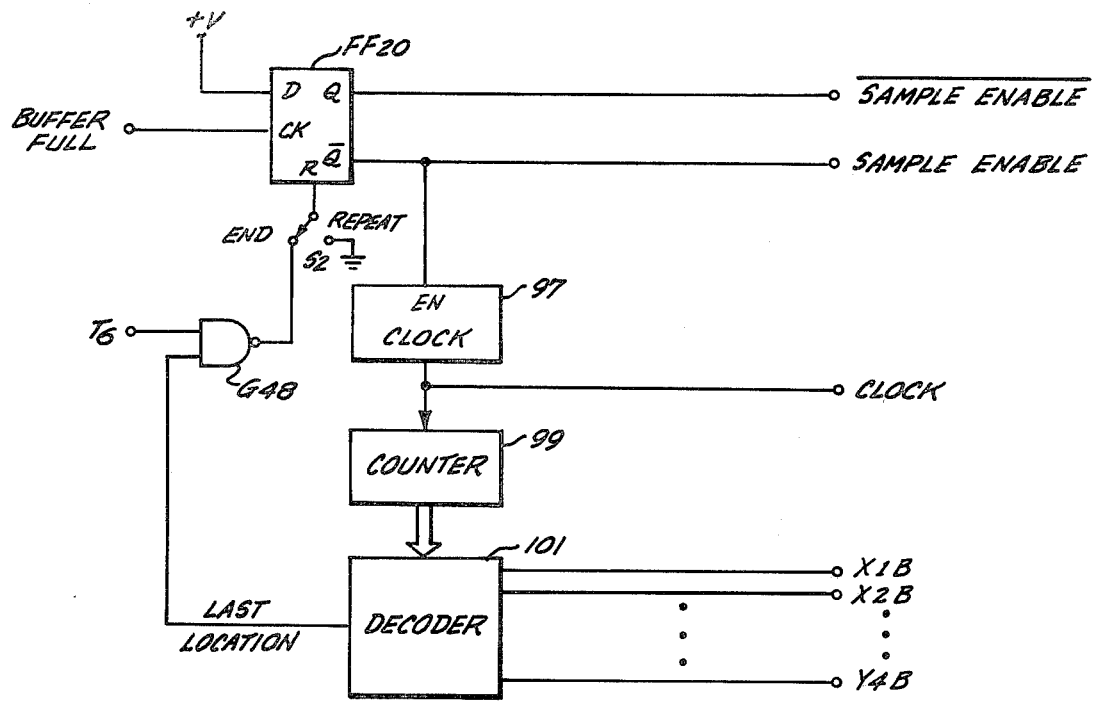
FIG. 10 is a block diagram of a readout address control suitable for use in the electronic subsystem illustrated in FIG. 3; and, FIG. 11 is a timing diagram used to assist in describing the readout mode of operation of the electronic subsystem illustrated in FIG. 3.

As will be better understood from the following discussion of FIG. 10, during the sample mode of operation, X1B, X2B, X3B, X4B, Y1B, Y2B, Y3B and Y4B are all high. As a result, the X1A, X2A, X3A, X4A, Y1A, Y2A, Y3A and Y4A signals control addressing of the RAM 95 via G40-G47. (Contrariwise, during the display mode of operation all of X1A-X4A and all of Y1A-Y4A are high, whereby X1B-X4B and Y1B-Y4B control the addressing of the RAM.)

In addition, during the sample mode of operation, at least one of X1A, X2A, X3A, X4A, Y1A, Y2A, Y3A and Y4A is low. As a result, the output of G39 is high, whereby G37 is enabled. Since G37 is enabled, a T3 pulse, which occurs subsequent to a T2 pulse, as previously described, via G38 enables the write input of the RAM 95. Consequently, subsequent to the presettable counter 91 (FIG. 8) being incremented by one as a result of the occurrence of a T2 pulse, the W0-W11 signals are written into the correct address of the RAM as a result of the occurrence of a T3 pulse.

The data register 93 (FIG. 9) reads the S0-S11 outputs of the RAM at the same time that the presettable counter 91 (FIG. 8) reads the output of the RAM, during the sample mode of operation, because the data register is also clocked by T2. More specifically, T2 clocks the data register during the sample mode of operation because $\overline{\text{SAMPLE ENABLE}}$ is low. Contrariwise, G33 (FIG. 9) is disabled by $\overline{\text{SAMPLE ENABLE}}$. Thus T4 pulses, should they occur, have no effect. Contrariwise, during the readout mode of operation T4 pulses clock the data register 93, as will be better understood from the following discussion of the readout address control.

In summary, during the sample mode of operation, a STROBE pulse occurs after the ANALOG VIDEO signal has been verified as analyzable and the appropriate FF4-FF19 flip-flops are set. The STROBE pulse causes a series of T1, T2 and T3 pulses to be produced by the timers. The T1 pulse causes the decoded output (C1-C15) of the FF4-FF19 flip-flops to be read and an appropriate X-Y address to be produced. The T2 pulse causes the count value stored at the X-Y address to be read out and incremented. The T2 pulse also causes the data register 93 to read the count value stored at the X-Y address. The T3 pulse causes the incremented count value to be read back into the same data bin. The T3 pulse also resets FF3 of the sample control (FIG. 4) and FF4-FF19 of the comparison system (FIG. 6).

FIG. 10 is a block diagram of a readout address control 61 (FIG. 3) suitable for use in the electronic subsystem illustrated in FIG. 3 and comprises: a D flip-flop designated FF20; a two-input NAND gate designated G48; a clock 97; and a counter 99; and a decoder 101.

The D input of FF20 is connected to a voltage source designated +V. The BUFFER FULL signal produced by the presettable counter 91 (FIG. 8) is applied to the clock input of FF20. The Q output of FF20 is the $\overline{\text{SAMPLE ENABLE}}$ signal applied to the data storage system illustrated in FIG. 9 and previously described. The $\overline{Q}$ output of FF20 is, thus, the SAMPLE ENABLE signal. In addition to being applied to the comparison system 53 and the sample address control 55, SAMPLE ENABLE is also applied to the enable input of the clock 97. The clock 97 produces negative going square wave CLOCK pulses. The CLOCK pulses are applied to the timers 63 (FIG. 3) and each CLOCK pulse is followed by a series of T4, T5, T6 positive going square wave signals, as illustrated in FIG. 11. More specifically, as illustrated in FIG. 11, immediately subsequent to the timers receiving a negative going square wave CLOCK pulse, a positive going square wave T4 pulse occurs. The T4 pulse is followed by a positive going square wave T5 pulse, which is followed by a positive going square wave T6 pulse.

The CLOCK pulses produced by the timer 97 are also applied to the counter 99. The output of the counter 99, which is in parallel form, is applied to decoder 101. The decoder 101 decodes the output of the counter, and in accordance therewith, sequentially produces the X1B, X2B, X3B, X4B, Y1B, Y2B, Y3B and Y4B readout address signals. More specifically, each CLOCK pulse increments the counter by one. Each such increment causes the X-Y output of the decoder to change to a new address. The X,Y/B addresses are, of course, similar to the X,Y/A addresses.

When the last X-Y address of the random access memory address sequence is produced by the decoder 101, a LAST LOCATION signal is applied by the decoder 101 to one input of G48 so as to enable G48. T6 is applied to the other input of G48. The output of G48 is applied to a remote input (denoted END) of a switch designated S2. The other remote terminal of S2 (denoted REPEAT) is connected to ground. The common terminal of S2 is connected to the reset input of FF20. As a result, if S2 is in the end position, the T6 pulse occurring after the LAST LOCATION signal has been produced resets FF20. Thus, SAMPLE ENABLE returns low and $\overline{\text{SAMPLE ENABLE}}$ returns high; and, the invention is returned to its sample mode of operation. On the other hand, if the movable contact of S2 is grounded via the REPEAT terminal, the sequence repeats, i.e., FF20 is not reset. Rather, the entire readout cycle is repeated as the counter 99 is clocked.

In summary, when BUFFER FULL shifts high, FF20 is clocked. As a result, $\overline{\text{SAMPLE ENABLE}}$ shifts from low to high and SAMPLE ENABLE shifts from high to low. Since SAMPLE ENABLE shifts from high to low, G32A (FIG. 6) is disabled whereby no further STROBE pulses are produced. In addition, OS5 (FIG. 7) is fired, whereby the sample address register 81 is cleared. When the sample address register 81 is cleared, the X1A-X4A, Y1A-Y4A address signals produced by the encoder 83 are all placed in a high state. As a result, the output of G39 (FIG. 9) shifts low, whereby G36 and G37 are disabled. Consequently, should any further T2 or T3 pulses occur, they will have no effect on the operation of the data storage system. Contrariwise, the shifting of $\overline{\text{SAMPLE ENABLE}}$ high enables G33, whereby subsequently occurring T4 pulses clock the data register 93. In addition, the shifting of SAMPLE ENABLE from high to low enables the clock 97 (FIG. 10). The clock 97, thereafter, produces CLOCK pulses. Each CLOCK pulse causes the timers 63 (FIG. 3) to sequentially produce a series of T4, T5 and T6 pulses, as illustrated in FIG. 11 and previously described. In addition, each CLOCK pulse causes the counter 99 (FIG. 10) to increment by one. As the counter output is incremented, the decoder 101 changes the X1B-X4B, Y1B-Y4B address signals. The decoder decodes the counter count values such that the fifteen RAM data bins in which data is stored are sequentially addressed. As the bins are addressed, the read output (S0-S11) of the random access memory 95 (FIG. 9) present the data stored in the addressed bins to the data register 93. Each new set of bin data is clocked into the data register 93 by the T4 pulse occurring after the CLOCK pulse creating an address change. As a result, the D0-D11 outputs of the data register sequentially carry the data stored in the bins of the random access memory 95. This data is converted from digital form into analog form by the digital-to-analog converter 95 (FIG. 3) and displayed by the display 67.

When the last bin is addressed, the decoder 101 (FIG. 10) produces a LAST LOCATION signal that enables G48. The next T6 signal then causes FF20 to be reset and the readout sequence of operation terminates. When FF20 is reset, SAMPLE ENABLE shifts from high to low and $\overline{\text{SAMPLE ENABLE}}$ shifts from low to high, whereby the particle size analyzer is returned to its sample mode of operation. During the readout sequence, all of the bins are cleared by T5 pulses causing the bins to read the W0-W11 output of the presettable counter 91 (FIG. 8), which was cleared when SAMPLE ENABLE shifted low at the start of the readout sequence, as previously described. Alternatively, if desired, the readout of data can be repeated, by placing S2 (FIG. 10) and S1 (FIG. 9) (which may be ganged together) in their REPEAT positions. In this case T5 pulses are not applied to the RAM, whereby bin data is not replaced by the W0-W11 output of the presettable counter. Moreover, FF20 (FIG. 10) is not reset by the T6 pulse following the last X1B-X4B, Y1B-Y4B address.

It will be appreciated from the foregoing description that the invention provides a particle size analyzer adapted to count the number of particles of a particular size detected by a laser anemometer and verified to be valid. Particle size is determined by measuring the intensity of the light scattered by the particle as it passes through the fringes forming the probe of the laser anemometer. The system provides an arrangement for verifying that the particle passes through an adequate number of fringes by determining whether or not an adequate number of "blinks" are present in the scattered light. Thus, not only does the preferred embodiment of the invention use the verification information produce by the laser anemometer, it also produces its own verification information. The invention provides a storage system having individual, particle size related bins that are incremented each time a particle falling within a bin related size is detected. When one of the bins reaches its maximum count value, the particle size analyzer is automatically shifted from a sample mode of operation to a readout mode of operation. In the readout mode of operation, all of the bin information is readout. As illustrated in FIG. 3, as the information is read out from the various bins, it is converted from digital form to analog form and then applied to a display. If desired, the display can be an oscilloscope display. Alternatively, the information can be applied to a storage medium, such as a magnetic tape recorder, for storage and display at a later time. Still further, the information can be stored as well as displayed.

While the preferred embodiment of the invention has been illustrated and described, it will be appreciated that various changes can be made therein without departing from the spirit and scope of the invention. For example, a comparison subsystem, other than one using operational amplifiers and clocked flip-flops, can be used, if desired. Further, rather than having the comparison system produce a high on only one of its outputs (and lows on all others), highs can be produced on all outputs and a low on only the related maximum level output. Still further, the comparison system output can be encoded in other manners. Also, the video signal, rather than the limiter signal, can be analyzed to determine if an adequate number of fringes have been intersected by a particle. In such an embodiment, the limiter signal need not be produced. Hence, the invention can be practiced otherwise than as specifically described herein.

The embodiments of the invention in which an exclusive property or privilege is claimed are defined as follows:

1. A particle size analyzer comprising:
   a crossed beam laser anemometer that produces a non-contacting probe formed of a series of fringes that produce blinking scattered light when a particle passes transversely through the series of fringes, detects the blinking scattered light produced by particles passing through said fringes and produces a fluctuating output signal having a magnitude related to the magnitude of the light scattered by particles passing through said fringes;
   analyzing means for: (a) receiving the fluctuating output signal of said crossed beam laser anemometer; (b) verifying that a particle causing a fluctuating output signal has passed through a number of fringes of said probe above a predetermined number; and (c) producing a coded output signal if the particle causing said fluctuating output signal has passed through said number of fringes, said coded output being a function of the magnitude of said fluctuating output signal;
   storage means, including a plurality of data bins, for: (a) receiving said coded output of said analyzing means; (b) reading out the data stored in a particular data bin each time a coded output occurs; (c) changing said data; and (d) writing the changed data back into the same data bin; and,
   readout means connected to said storage means for sequentially reading out the data stored in said data bins.

2. A particle size analyzer as claimed in claim 1 wherein said analyzing means verifies that the particle causing said fluctuating output signal has passed through said number of fringes by analyzing the number of fluctuations of said fluctuating output signal.

3. A particle size analyzer as claimed in claim 2 wherein the analysis of the number of fluctuations of said fluctuating output signal is done by counting the fluctuations of said fluctuating output signal and comparing the resultant count value with a set value equal to said number of fringes.

4. A particle size analyzer as claimed in claim 3 wherein said analyzing means includes a comparison system that measures the intensity of said fluctuating output signal by stepwise comparing the magnitude of said fluctuating output signal with step related reference voltages, decoding the results of said stepwise comparison and producing said coded output in accordance therewith.

5. A particle size analyzer as claimed in claim 4 wherein said storage means includes:
   a sample address control connected to said comparison system for receiving said coded output and producing, in accordance therewith, an address signal;
   a data storage system, including said plurality of data bins, connected to said sample address control for receiving said address signals and producing the data stored in a data bin related to an address signal produced by said sample address control; and,
   a data update control connected to said data storage system for receiving the data from the data bin addressed by the output of said sample address control, incrementing said data and storing said incremented data in the same data bin that produced said data.

6. A particle size analyzer as claimed in claim 5 wherein said fluctuating output signal of said laser anemometer includes two fluctuating components, one of said fluctuating components being a video signal whose magnitude is related to the magnitude of the light scattered by a particle passing through said probe and the other of said fluctuating components being a square wave signal that tracks the fluctuations of said video signal.

7. A particle size analyzer as claimed in claim 6 wherein said analyzing means also includes a sample control, said sample control adapted to receive and buffer said video signal and apply said video signal to said comparison system, said sample control also including counting means for counting the fluctuations of said square wave signal and comparing the resultant count value with said set value equal to said number of fringes, said sample control also including sample control means for producing a sample signal if the number of fluctuations counted by said counting means reaches a level equal to said set value equal to said number of fringes, said sample signal being applied to said sample address control for enabling said sample address control to receive said coded output and produce, in accordance therewith, said address signal.

8. A particle size analyzer as claimed in claim 7 wherein said readout means includes a readout address control for producing and applying to said data storage system address signals related to the addresses of said plurality of data bins included in said data storage system and converter means for receiving data stored in said plurality of data bins of said data storage system as said data bins are addressed and converting said received data into a form suitable for receipt by a display or recording medium.

9. A particle size analyzer as claimed in claim 8 wherein said data storage system includes means for selectively receiving said address signals produced by said sample address control and said readout address control and using said address signals to control the data read out from said data bins.

10. A particle size analyzer as claimed in claim 1 wherein read out data is changed by incrementing said read out data.

11. A particle size analyzer as claimed in claim 1 wherein said analyzing means includes a comparison system that measures the intensity of said fluctuating output signal by stepwise comparing the magnitude of said fluctuating output signal with step related reference voltages, decoding the results of said stepwise comparison and producing said coded output in accordance therewith.

12. A particle size analyzer as claimed in claim 11 wherein said storage means includes:
   a sample address control connected to said comparison system for receiving said coded output and producing, in accordance therewith, an address signal;
   a data storage system, including a plurality of data bins, connected to said sample address control for receiving said address signals and producing the data stored in a data bin related to an address signal produced by said sample address control; and,
   a data update control connected to said data storage system for receiving the data from the data bin addressed by the output of said sample address control, incrementing said data and storing said incremented data in the same data bin that produced said data.

13. A particle size analyzer as claimed in claim 12 wherein said fluctuating output signal of said laser anemometer includes two fluctuating components, one of said fluctuating components being a video signal whose magnitude is related to the magnitude of the light scattered by a particle passing through said probe and the other of said fluctuating components being a square wave signal that tracks the fluctuations of said video signal.

14. A particle size analyzer as claimed in claim 13 wherein said analyzing means also includes a sample control, said sample control adapted to receive and buffer said video signal and apply said video signal to said comparison system, said sample control also including counting means for counting the fluctuations of said square wave signal and comparing the resultant count value with said set value equal to said number of fringes, said sample control also including sample control means for producing a sample signal if the number of fluctuations counted by said counting means reaches a level equal to or greater than said set value equal to said number of fringes, said sample signal being applied to said sample address control for enabling said sample address control to receive said coded output and produce, in accordance therewith, said address signal.

15. A particle size analyzer as claimed in claim 14 wherein said readout means includes a readout address control for producing and applying to said data storage system address signals related to the addresses of said plurality of data bins included in said data storage system and converter means for receiving data stored in said plurality of data bins of said data storage system as said data bins are addressed and converting said received data into a form suitable for receipt by a display or recording medium.

16. A particle size analyzer as claimed in claim 15 wherein said data storage system includes means for selectively receiving said address signals produced by said sample address control and said readout address control and using said address signals to control the data read out from said data bins.

* * * * *